United States Patent
Liu et al.

(10) Patent No.: US 8,834,021 B2
(45) Date of Patent: Sep. 16, 2014

(54) DIGITAL X-RAY DETECTOR WITH A MULTI-FUNCTIONAL PANEL SUPPORT

(75) Inventors: James Zhengshe Liu, Glenview, IL (US); Habib Vafi, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 441 days.

(21) Appl. No.: 13/198,206

(22) Filed: Aug. 4, 2011

(65) Prior Publication Data
US 2013/0034215 A1    Feb. 7, 2013

(51) Int. Cl.
*H01L 27/146* (2006.01)
*A61B 6/00* (2006.01)
*A61B 6/10* (2006.01)

(52) U.S. Cl.
CPC .............. *A61B 6/4233* (2013.01); *A61B 6/107* (2013.01); *A61B 6/56* (2013.01)
USPC ...................................... 378/189; 250/370.09

(58) Field of Classification Search
USPC .......................... 378/19, 189–192, 204, 210; 250/370.01, 370.08, 370.09, 370.11, 250/370.102, 370.13, 370.104, 370.15, 526, 250/370.12, 370.14
See application file for complete search history.

(56) References Cited

U.S. PATENT DOCUMENTS

| | | | |
|---|---|---|---|
| 6,069,935 A | 5/2000 | Schick et al. | |
| 6,475,664 B1 * | 11/2002 | Kawakami et al. | 429/137 |
| 7,247,859 B2 * | 7/2007 | Murphy et al. | 250/370.09 |
| 7,495,226 B2 * | 2/2009 | Jadrich et al. | 250/370.09 |
| 2006/0065846 A1 | 3/2006 | Ertel et al. | |
| 2007/0272873 A1 | 11/2007 | Jadrich et al. | |
| 2008/0224056 A1 | 9/2008 | Liu et al. | |
| 2009/0207974 A1 | 8/2009 | Yi | |
| 2010/0108898 A1 | 5/2010 | Zhang et al. | |
| 2013/0032696 A1 | 2/2013 | Tajima | |

FOREIGN PATENT DOCUMENTS

WO    2011036901 A1    3/2011

OTHER PUBLICATIONS

PCT/US/2012/047390; International Search Report, mailed Nov. 7, 2012, 12 pages.
U.S. Appl. No. 13/010,982, filed Jan. 21, 2011, Liu et al.
U.S. Appl. No. 13/011,016, filed Jan. 21, 2011, Liu et al.
U.S. Appl. No. 13/011,033, filed Jan. 21, 2011, Liu et al.
U.S. Appl. No. 13/095,655, filed Apr. 27, 2011, Liu et al.
U.S. Appl. No. 61/502,286, filed Jun. 28, 2011, Petrick.
International Search Report and Written Opinion PCT/US/2013/021091 Mailed on Jun. 7, 2013.

* cited by examiner

*Primary Examiner* — Anastasia Midkiff
(74) *Attorney, Agent, or Firm* — Fletcher Yoder, P.C.

(57) ABSTRACT

A digital X-ray detector includes a multi-functional panel support configured to support a digital detector array on a first side of the panel support and electronics on a second side of the panel support. The panel support includes a first enclosure and a rechargeable battery disposed within the first enclosure.

24 Claims, 4 Drawing Sheets

DIGITAL X-RAY DETECTOR WITH A MULTI-FUNCTIONAL PANEL SUPPORT

BACKGROUND OF THE INVENTION

The subject matter disclosed herein relates to X-ray imaging systems, and particularly to a panel support of a digital X-ray detector of such systems.

A number of radiological imaging systems of various designs are known and are presently in use. Such systems generally are based upon generation of X-rays that are directed toward a subject of interest. The X-rays traverse the subject and impact a film or a digital detector. In medical diagnostic contexts, for example, such systems may be used to visualize internal tissues and diagnose patient ailments. In other contexts, parts, baggage, parcels, and other subjects may be imaged to assess their contents and for other purposes.

Increasingly, such X-ray systems use digital circuitry, such as solid-state detectors, for detecting the X-rays, which are attenuated, scattered, or absorbed by the intervening structures of the subject. Solid-state detectors may generate electrical signals indicative of the intensities of received X-rays. These signals, in turn, may be acquired and processed to reconstruct images of the subject of interest.

Conventional construction of digital X-ray detectors results in a relatively heavy and thick digital X-ray detector in part due to multiple components housed within the detector, where each component is designed to perform one or more specific functions. However, as digital X-ray imaging systems have become increasingly widespread, digital X-ray detectors have become more portable for even greater versatility. With the advent of portable digital X-ray detectors comes a need for lighter, thinner, smaller detectors that retain the same imager size.

BRIEF DESCRIPTION OF THE INVENTION

In accordance with one embodiment, a digital X-ray detector includes a multi-functional panel support configured to support a digital detector array on a first side of the panel support and electronics on a second side of the panel support. The panel support includes a first enclosure and a rechargeable battery disposed within the first enclosure.

In accordance with another embodiment, a digital X-ray detector includes a multi-functional panel support configured to support a digital detector array on a first side of the panel support and electronics on a second side of the panel support. The panel support includes a first enclosure, a power source disposed within the first enclosure, a second enclosure surrounding the first enclosure, and a support layer disposed between the first and second enclosures.

In accordance with a further embodiment, a digital X-ray detector includes a multi-functional panel support configured to support a digital detector array and electronics, to provide power to the detector, and to protect the electronics from radiation damage.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

Figure 1:
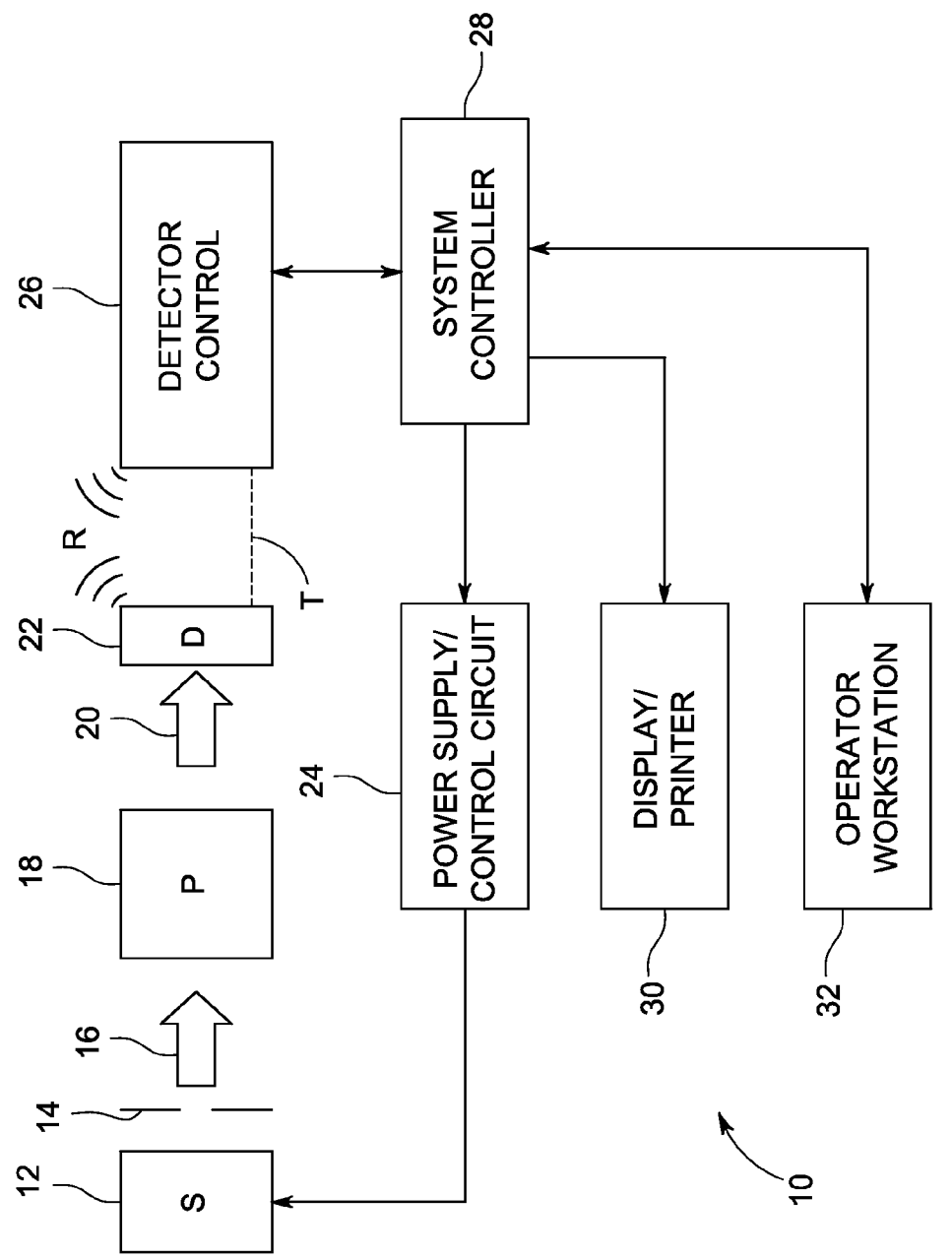
FIG. 1 is a diagrammatical overview of an exemplary digital X-ray imaging system in which the present technique may be utilized.

Turning now to the drawings, FIG. 1 illustrates diagrammatically an imaging system 10 for acquiring and processing discrete pixel image data. The imaging system 10 may be a fixed or mobile imaging system. In the illustrated embodiment, the imaging system 10 is a digital X-ray system designed both to acquire original image data and to process the image data for display in accordance with the present technique. In certain embodiments, the X-ray system 10, as adapted, may be a digital X-ray system. Throughout the following discussion, however, while basic and background information is provided on the digital X-ray system used in medical diagnostic applications, it should be borne in mind that aspects of the present techniques may be applied to digital detectors, including X-ray detectors, used in different settings (e.g., projection X-ray, computed tomography imaging, tomosynthesis imaging, etc.) and for different purposes (e.g., parcel, baggage, vehicle and part inspection, etc.).

In the embodiment illustrated in FIG. 1, the imaging system 10 includes a source of X-ray radiation 12 positioned adjacent to a collimator 14. The collimator 14 permits a stream of radiation 16 to pass into a region in which an object or subject, such as a patient 18, is positioned. A portion of the radiation 20 passes through or around the subject and impacts a digital X-ray detector, represented generally at reference numeral 22. As will be appreciated by those skilled in the art, the detector 22 may convert the X-ray photons received on its surface to lower energy photons, and subsequently to electric signals, which are acquired and processed to reconstruct an image of the features within the subject.

The radiation source 12 is controlled by a power supply/control circuit 24 which supplies both power and control signals for examination sequences. Moreover, the detector 22 is communicatively coupled to a detector controller 26 which commands acquisition of the signals generated in the detector 22. In the presently illustrated embodiment, the detector 22 (e.g., wireless detector) may communicate with the detector controller 26 via any suitable wireless communication standard, although the use of detectors 22 that communicate with the detector controller 26 through a cable or some other mechanical connection are also envisaged. In certain embodiments, the detector controller 26 may be disposed within the detector 22. The detector controller 26 may also execute various signal processing and filtration functions, such as for initial adjustment of dynamic ranges, interleaving of digital image data, and so forth.

Both the power supply/control circuit 24 and the detector controller 26 are responsive to signals from a system controller 28. In general, the system controller 28 commands operation of the imaging system to execute examination protocols and to process acquired image data. In the present context, the system controller 28 also includes signal processing circuitry, typically based upon a programmed general purpose or application-specific digital computer; and associated memory circuitry, such as optical memory devices, magnetic memory devices, or solid-state memory devices. The memory circuitry allows for storing programs and routines executed by a processor of the computer to carry out various functionalities, as well as for storing configuration parameters and image data; interface circuits; and so forth.

In the embodiment illustrated in FIG. 1, the system controller 28 is linked to at least one output device, such as a display or printer, as indicated at reference numeral 30. The output device may include standard or special purpose computer monitors and associated processing circuitry. One or more operator workstations 32 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

As mentioned above, the imaging system 10 may be a conventional analog imaging system, retrofitted for digital image data acquisition and processing. For example, the imaging system 10 may be an analog system utilizing a digital X-ray detector 22 configured to acquire image data without communication from a source controller and, thus, without a priori knowledge of beginning and ending times of an X-ray exposure. Systems and methods for using the digital X-ray detector 22 with an analog imaging system may be found in U.S. patent application Ser. No. 13/010,982, filed Jan. 21, 2011, entitled "X-RAY SYSTEM AND METHOD WITH DIGITAL IMAGE ACQUISTION," U.S. patent application Ser. No. 13/011,016, filed Jan. 21, 2011, entitled "X-RAY SYSTEM AND METHOD FOR PRODUCING X-RAY IMAGE DATA," and U.S. patent application Ser. No. 13/011,033, filed Jan. 21, 2011, entitled "X-RAY SYSTEM AND METHOD FOR SAMPLING IMAGE DATA," all of which are herein incorporated by reference in their entirety for all purposes.

Figure 2:
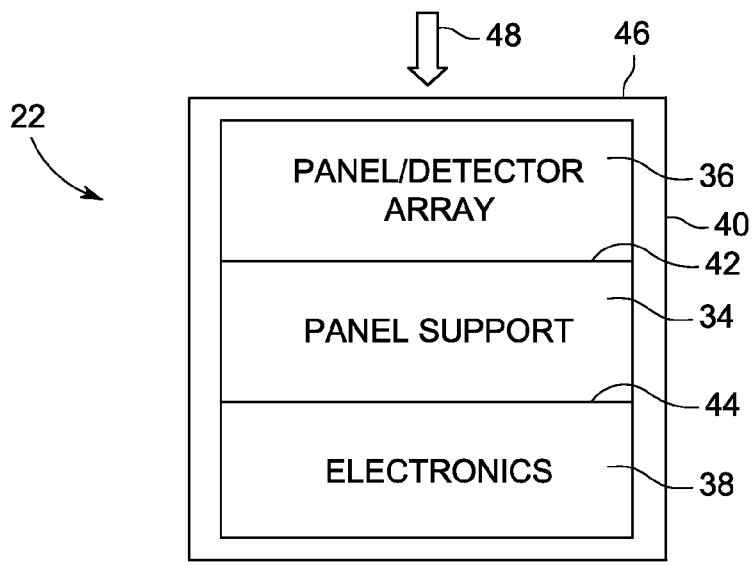
FIG. 2 is a diagrammatical representation of components in a detector of the system of FIG. 1.

Referring now to FIG. 2, a diagrammatical representation of a digital X-ray detector 22 having a multi-purpose panel support 34 is illustrated. The detector 22 includes a panel or digital detector array 36, the panel support 34 (e.g., multi-purpose panel support), electronics 38, and a shell assembly or enclosure 40 surrounding the array 36, panel support 34, and electronics 38. The panel support 34 is configured to perform multiple functions. For example, the panel support 34 is configured to support the digital detector array 36 and the electronics 38. In particular, the panel support 34 supports the digital detector array 36 on a first side 42 of the support 34 and the electronics 38 on a second side 44 of the support 34. Specifically, the panel support 34 mechanically isolates the imaging components of the digital detector array 36 from the electronics 38. In addition, the panel support 34 powers the detector 22. For example, the panel support 34 may internally house a power source (e.g., rechargeable battery). Further, the panel support 34 protects the power source and electronics from radiation damage. Yet further, the panel support 34 attenuates residual X-rays that pass through the digital detector array 36 to reduce backscattering. In certain embodiments, the panel support 34 may provide electromagnetic interference (EMI) shielding. By performing multiple functions, the panel support 34 enables the detector 22 to be lighter and thinner. Also, in certain embodiments, the panel or digital detector array 36 may also be thinner to enable the detector 22 to be lighter and thinner as described in greater detail below.

As to other components of the digital detector 22, the electronics 38 control the operation of the detector 22. In particular, electronics 38 enable the acquisition of image data from the digital detector array 36. The electronics 38 may include circuit boards, data modules, scanning modules, and other circuitry.

The panel or digital detector array 36 may include an imaging panel and detector panel. In certain embodiments, the detector panel may be thinner to enable the detector 22 to be lighter and thinner as described in greater detail below. The imaging panel may include a scintillator layer for converting incident X-rays to visible light. The scintillator layer, which may be fabricated from cesium iodide (CsI) or other scintillating materials, is designed to emit light proportional to the energy and the amount of the X-rays absorbed. As such, light emissions will be higher in those regions of the scintillator layer where either more X-rays were received or the energy level of the received X-rays was higher. Since the composition of the subject will attenuate the X-rays projected by the X-ray source to varying degrees, the energy level and the amount of the X-rays impinging upon the scintillator layer will not be uniform across the scintillator layer. This variation in light emission will be used to generate contrast in the reconstructed image.

The light emitted by the scintillator layer is detected by a photosensitive layer on the detector panel. The photosensitive layer includes an array of photosensitive elements or detector elements to store an electrical charge in proportion to the quantity of incident light absorbed by the respective detector elements. Generally, each detector element has a light sensitive region and a region including electronics to control the storage and output of electrical charge from that detector element. The light sensitive region may be composed of a photodiode, which absorbs light and subsequently creates and stores electronic charge. After exposure, the electrical charge in each detector element is read out using logic-controlled electronics 38.

Each detector element is generally controlled using a transistor-based switch. In this regard, the source of the transistor is connected to the photodiode, the drain of the transistor is connected to a readout line, and the gate of the transistor is connected to a scan control interface disposed on the electronics 38 in the detector 22. When negative voltage is applied to the gate, the switch is driven to an OFF state, thereby preventing conduction between the source and the drain. Conversely, when a positive voltage is applied to the gate, the switch is turned ON, thereby allowing the photodiode to be recharged, with the amount of charge being a function of the diode depletion as an indication of incident energy, which is detected on the readout line. Each detector element of the detector array 36 is constructed with a respective transistor (e.g., a thin-film transistor).

Specifically during exposure to X-rays, negative voltage is applied to all gate lines resulting in all the transistor switches being driven to or placed in an OFF state. As a result, any charge depletion experienced during exposure reduces the charge of each detector element. During read out, positive voltage is sequentially applied to each gate line. That is, the detector is an X-Y matrix of detector elements and all of the gates of the transistors in a line are connected together so that turning ON one gate line simultaneously reads out all the detector elements in that line. A multiplexer may also be used to support read out of the detector elements in a faster fashion. The output of each detector element is then input to an output circuit (e.g., a digitizer) that digitizes the acquired signals for subsequent image reconstruction on a per pixel basis. In a typical reconstruction, each pixel of the reconstructed image corresponds to a single detector element of the digital detector array 36.

The enclosure 40 protects the fragile detector components from damage when exposed to an external load or an impact. The enclosure 40 includes a front side 46 to receive radiation 48. The enclosure 40 may be formed of materials such as a metal, a metal alloy, a plastic, a composite material, or a combination of the above. In certain embodiments, the material has low X-ray attenuation characteristics. In one embodiment, the enclosure 40 may be formed of a lightweight, durable composite material such as a carbon fiber reinforced plastic material, carbon reinforced plastic material in combination with foam cores, or a graphite fiber-epoxy composite. Some embodiments may include one or more material compositions having a non-conductive matrix with conductive elements disposed therein, and may provide electromagnetic interference shielding to protect the internal components of the detector 22 from external electronic noise. Additionally, the enclosure 40 may be designed to be substantially rigid with minimal deflection when subjected to an external load.

Figure 3:
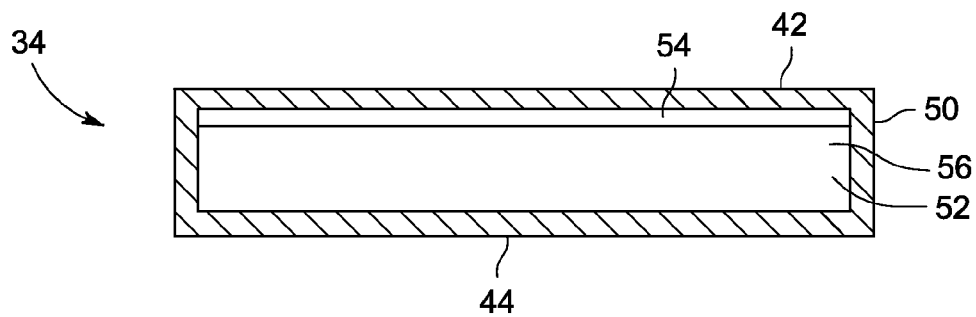
FIG. 3 is a diagrammatical representation of a multi-functional panel support of the detector of FIG. 2 having a single enclosure.

FIGS. 3-7 illustrate embodiments of the multi-functional panel support 34. As illustrated in FIG. 3, the panel support 34 includes an enclosure 50, a power source 52, and compressible layer 54 disposed within the enclosure 50. The enclosure 50 surrounds both the power source 52 and the compressible layer 54. In the illustrated embodiment, the enclosure 50 includes the first side 42 to support the digital detector array 36 and the second side 44 to support the electronics 38. The compressible layer 54 is disposed between the first side 42 of the panel support 34 and the power source 52. In certain embodiments, the power source 52 may include a rechargeable battery 56. The rechargeable battery 56 may include a plurality of battery cells. For example, as illustrated, the plurality of battery cells may be stacked to form a rectangular prism. Alternatively, each battery cell may be rolled into a cylinder and the rechargeable battery 56 may include a plurality of cylindrical battery cells (see FIG. 8).

The compressible layer 54 enables the power source 52 (e.g., rechargeable battery 56) to expand within the enclosure 50 during charge and discharge of the power source 52. In certain embodiments, the compressible layer 54 absorbs X-rays to protect the power source 52 and electronics 38 beneath the compressible layer 54 from radiation damage. In further embodiments, the compressible layer 54 reduces the backscatter of residual X-rays that pass through the panel or digital detector array 36. The compressible layer 54 may be formed of a metal such as lead, tungsten, or a combination thereof.

Generally, the enclosure 50 may be formed of a metal, a metal alloy, a plastic, a composite material, or a combination of the above material. In one embodiment, the enclosure 50 may be substantially formed of a carbon fiber reinforced plastic material or a graphite fiber-epoxy composite. The composite materials are typically combinations of a reinforcement and a matrix. The matrix material, such as a resin or epoxy, surrounds and supports the reinforcement material. The resins used could be thermosets or thermoplastics. The reinforcement materials, such as an organic or inorganic fibers or particles, are bound together by the composite matrix. For fiber reinforcements, the direction the individual fibers may be oriented to control the rigidity and the strength of the composite. Further, composite may be formed of several individual layers with the orientation or alignment of the reinforcement layers varying through the thickness of composite. Also, the layers of the composite could use multiple materials (carbon, Kevlar, aluminum foil etc.) in different forms (particles, fibers, fabric, thin foils etc.).

Figure 4:
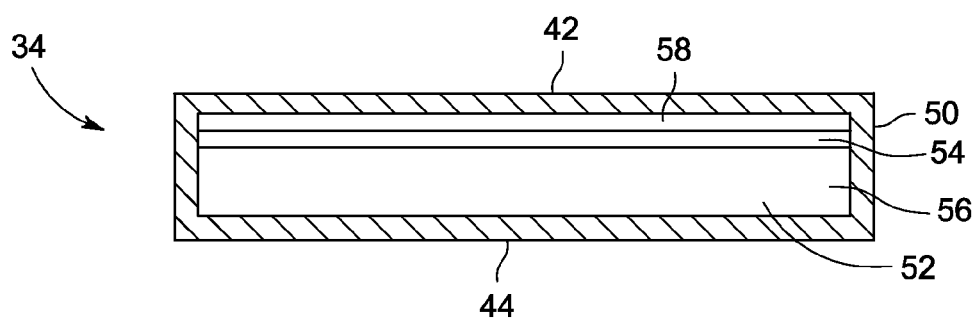
FIG. 4 is a diagrammatical representation of the multi-functional panel support of FIG. 3 having a magnetic shielding layer.

In certain embodiments, the panel support 34 may also include a magnetic shielding layer 58 as illustrated in FIG. 4. As illustrated, the magnetic shielding layer 58 is disposed between the first side 42 of the panel support 34 and the compressible layer 54. The internal electronics 38 of the digital detector may be susceptible to interference from external electronic devices, and such external devices may also be affected by the electronic noise generated by the internal electronics 38 of the digital detector 22. The magnetic shielding layer 58 shields the internal components from EMI. In particular, the magnetic shielding layer 58 and, thus, the panel support 34 provides EMI shielding to the detector 22. The magnetic shielding layer 58 may consists of a metal such as aluminum or copper or a metallic alloy such as a nickel-iron alloy (e.g., Amumetal™) to improve the EMI sustainability of the detector 22.

Figure 5:
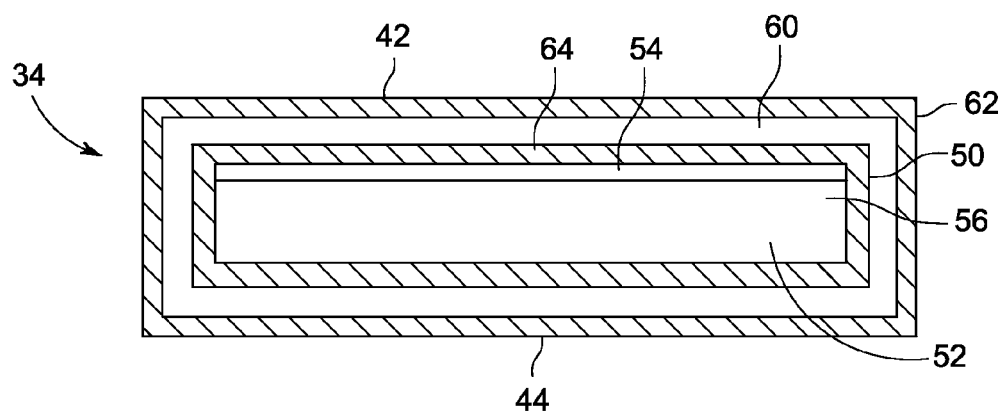
FIG. 5 is a diagrammatical representation of a multi-functional panel support of the detector of FIG. 2 having multiple enclosures.
Figure 6:
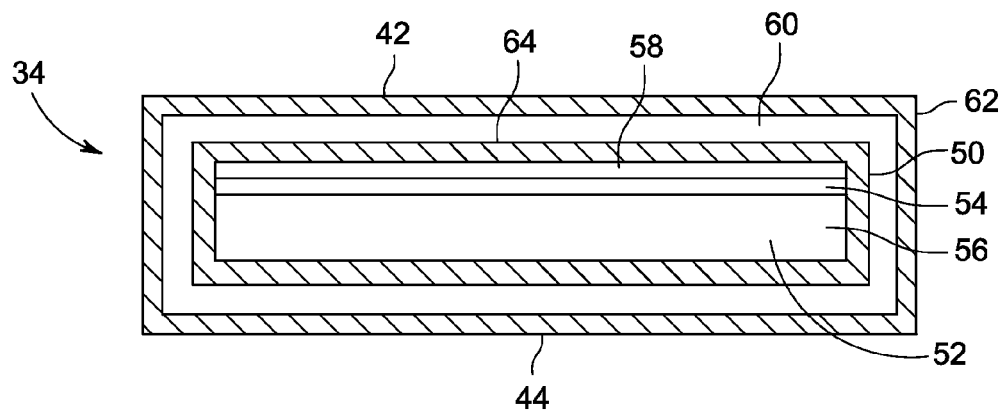
FIG. 6 is a diagrammatical representation of the multi-functional panel support of FIG. 5 having a magnetic shielding layer.

In certain embodiments, the panel support 34 may include a sandwich type construction as illustrated in FIG. 5. As illustrated, the panel support 34 includes a support layer 60 disposed between enclosures 50 and 62. The enclosure 62 surrounds the enclosure 50. The enclosure 62 includes the first and second sides 42 of the panel support 34. In particular, the enclosure 62 includes the first side 42 to support the digital detector array 36 and the second side 44 to support the electronics 38. The panel support 34 also includes a compressible layer 54, as described above, disposed between the first side 42 of the panel support 34 (and side 62 of the enclosure 50) and the power source 52. In certain embodiments, the panel support 34 with the sandwich type construction may include the magnetic shielding layer 58 described above disposed between the first side 42 of the panel support 34 (and side 64 of the enclosure 50) and the compressible layer 54 as illustrated in FIG. 6.

The sandwich type construction provides a lightweight yet stiff assembly for the support panel 34. In particular, the support layer 60 disposed between the enclosures 50 and 62 provides greater mechanical stiffness and improved energy absorption capability. The support layer 60 may include fine-celled, low density polymethacrylimide foam. For example, the support layer 60 may include Rohacell® foam manufactured by Evonik Industries, Essen, Germany. Alternatively, the foam layer 60 may include fine-celled, low compression-set, high density polyurethane foams and/or a high density, flexible, microcellular urethane foam materials. Although these foams are described as high density, the support layer 60 is generally low density as compared with other materials. For example, in some embodiments, the support layer 60 may include CONFOR® foam and/or ISOLOSS® foam manufactured by E-A-R Specialty Composites, a business unit of Aearo Technologies, Indianapolis, Ind. In other embodiments, the support layer 60 may include PORON® foam manufactured by Rogers Corporation, Rogers, Conn. The enclosures 50 and 62 may be formed from the materials described above in FIG. 3.

Figure 7:
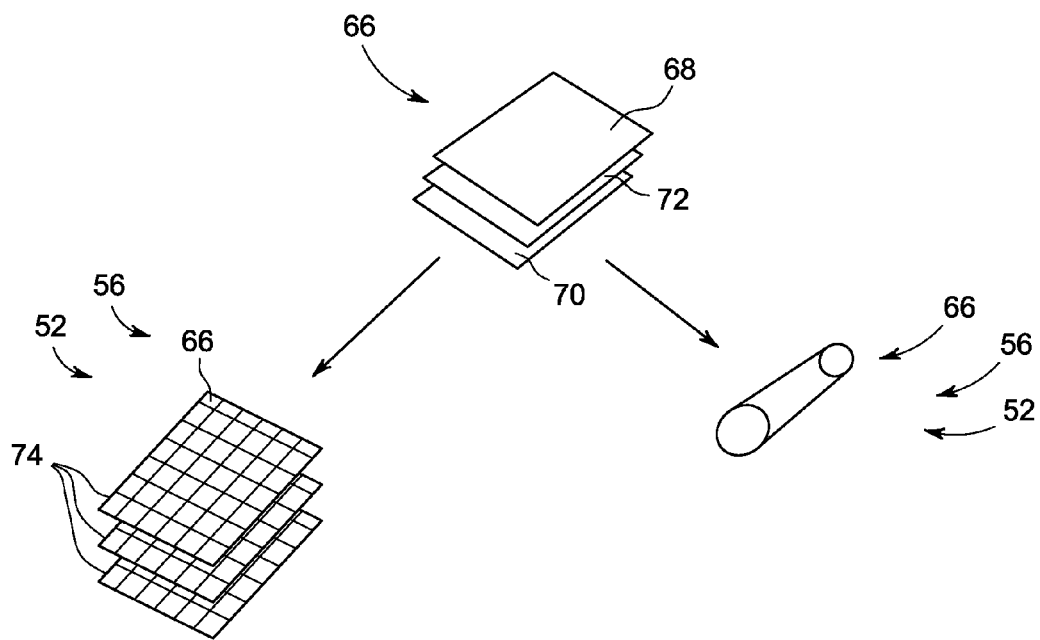
FIG. 7 is a diagrammatical representation of rechargeable battery cells utilized within the multi-functional panel support.

As mentioned above, the power source 52 include a rechargeable battery 56 (e.g., lithium ion battery) formed by a plurality of battery cells. FIG. 7 illustrates the structure of the battery cells 66 that form the rechargeable battery 56 in the panel support 34. Each battery cell 66 includes an anode 68, a cathode 70, and an electrolyte 72 disposed between the anode 68 and cathode 70 stacked together. Generally, the anode 58 may be formed of graphite. The cathode 70 may be formed of lithium cobalt oxide, a polyanion (e.g., lithium iron phosphate), or spinel (e.g., lithium manganese oxide). The electrolyte 72 may be formed of a mixture of organic carbonates such as ethylene carbonate or diethyl carbonate that include complexes of lithium ions. In certain embodiments, the plurality of battery cells 66 may be formed into sheets 74 of battery cells 66. These sheets 74 of battery cells 66 may be stacked together to form a rectangular prism (see FIGS. 3-6). In another embodiment, the battery cell 66 may be rolled into a cylindrical battery cell 66.

Figure 8:
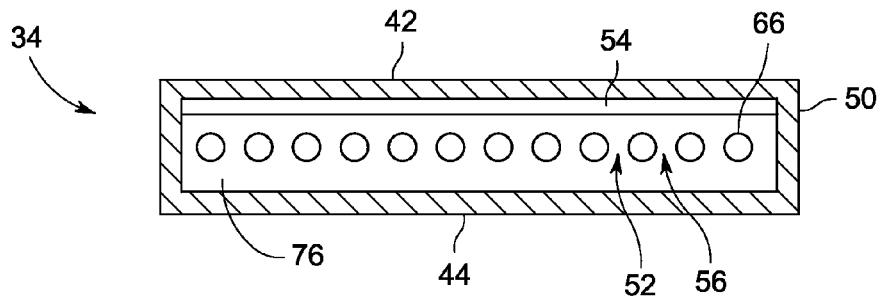
FIG. 8 is a diagrammatical representation of a multi-functional panel support of the detector of FIG. 2 having cylindrical battery cells.

The plurality of cylindrical battery cells 66 may be disposed within the panel support 34 as illustrated in FIG. 8. The panel support 34 is as described in FIG. 3 except, instead of a rectangular prism-shaped rechargeable battery 56, the battery 56 includes a plurality of cylindrical battery cells 66. The cylindrical battery cells 66 are disposed within a soft core layer 76 made of materials similar to those described above for support layer 60. As above, the soft core layer 76 provides a stiff assembly to the panel support 34. In addition, the soft core layer 76 enables the battery cells to expand during charge and discharge. The plurality of cylindrical battery cells 66 may also be utilized in embodiments of the panel support 34 described above that include the magnetic shielding layer and/or sandwich type construction (see FIGS. 4-6).

Figure 9:
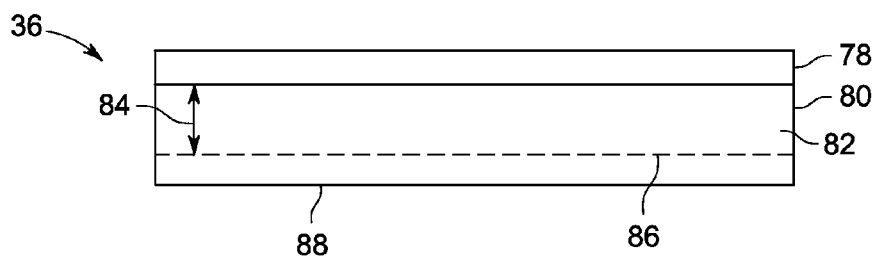
FIG. 9 is a diagrammatical representation of a digital detector array of the detector.

As mentioned above, in certain embodiments, the panel or digital detector array 36 may be thinner to enable the detector 22 to be lighter and thinner. As illustrated in FIG. 9, the detector array 36 includes an imaging panel 78 and a detector panel 80. The imaging panel 78 may include a scintillator layer as described above. The detector panel 80 may include a photosensitive layer as described above. In addition, the detector panel 80 includes a glass layer 82. In the illustrated embodiment, a width 84 of the glass layer 82 is less than approximately 0.6 mm In certain embodiments, the width 84 may be approximately 0.1 mm or less. For example, the width 84 of the glass layer 84 may range from approximately 0.01 mm to less than 0.6 mm, 0.1 mm to 0.6 mm, 0.2 mm to 0.5 mm, 0.3 mm to 0.4 mm, 0.05 mm to 0.1 mm, and all subranges therebetween. In certain embodiments, the detector panel 80 may also include an adhesive layer 86 located on a side 88 of the detector array 36 that couples or adheres the panel 80 to the side 42 of the multi-functional panel support 34. The adhesive layer 86 may include adhesive (e.g., glue) and/or epoxy resin. In particular, the components of the adhesive layer 86 may be configured to withstand temperatures of at least 200° C. during panel processing.

Technical effects of the disclosed embodiments include providing lighter and thinner digital X-ray detectors 22. In particular, the detector 22 includes a multi-purpose panel support 34 that enables multiple functions in a single component (i.e., the support 34) as opposed to multiple components of the detector 22. For example, the multi-panel support 34 may provide support to both the panel 36 and electronics 38, power to the detector 22, reduce backscattering of X-rays, and provide EMI shielding. In certain embodiments, the panel support 34 may include a sandwich type construction to provide greater mechanical stiffness and improved energy absorption capability to the detector 22. By incorporating multiple functions into the multi-panel support 34, the detector 22 may be built with a lighter and thinner construction.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A digital X-ray detector, comprising:
a multi-functional panel support configured to be disposed within a shell assembly of the detector and to support a digital detector array on a first side of the panel support and electronics on a second side of the panel support, wherein the panel support comprises a first enclosure configured to be completely enclosed within the shell assembly and a rechargeable battery disposed within the first enclosure.

2. The detector of claim 1, wherein the panel support comprises a compressible layer disposed between the first side of the panel support and the rechargeable battery, and the compressible layer is configured to enable the rechargeable battery to expand within the first enclosure.

3. The detector of claim 2, wherein the compressible layer is configured to absorb X-rays to protect the rechargeable battery and electronics from radiation damage.

4. The detector of claim 2, wherein the compressible layer is configured to reduce backscattering of X-rays.

5. The detector of claim 2, wherein the panel support comprises a magnetic shielding layer disposed between the first side of the panel support and the compressible layer.

6. The detector of claim 1, wherein the panel support comprises a second enclosure configured to be completely enclosed within the shell assembly surrounding the first enclosure and a support layer disposed between the first and second enclosures.

7. The detector of claim 6, wherein the panel support comprises a compressible layer disposed between the first side of the panel support and the rechargeable battery, and the compressible layer is configured to enable the rechargeable battery to expand within the first enclosure.

8. The detector of claim 7, wherein the compressible layer is configured to absorb X-rays to protect the rechargeable battery and electronics from radiation damage.

9. The detector of claim 7, wherein the compressible layer is configured to reduce backscattering of X-rays.

10. The detector of claim 7, wherein the panel support comprises a magnetic shielding layer disposed between the first side of the panel support and the compressible layer.

11. The detector of claim 1, wherein the rechargeable battery comprises a plurality of stacked battery cells that form a rectangular prism or a plurality of cylindrical battery cells.

12. A digital X-ray detector, comprising:
a multi-functional panel support configured to be disposed within a shell assembly of the detector and to support a digital detector array on a first side of the panel support and electronics on a second side of the panel support, wherein the panel support comprises a first enclosure configured to be completely enclosed within the shell assembly, a power source disposed within the first enclosure, a second enclosure surrounding the first enclosure, and a support layer disposed between the first and second enclosures.

13. The detector of claim 12, wherein the panel support comprises a compressible layer disposed between the first side of the panel support and the power source, and the compressible layer is configured to enable the power source to expand within the first enclosure.

14. The detector of claim 13, wherein the compressible layer is configured to absorb X-rays to protect the power source and electronics from radiation damage.

15. The detector of claim 13, wherein the compressible layer is configured to reduce backscattering of X-rays.

16. The detector of claim 13, wherein the panel support comprises a magnetic shielding layer disposed between the first side of the panel support and the compressible layer.

17. The detector of claim 12, wherein the power source comprises a rechargeable battery.

18. The detector of claim 17, wherein the rechargeable battery comprises a plurality of stacked battery cells that form a rectangular prism.

19. The detector of claim 17, wherein the rechargeable battery comprises a plurality of cylindrical battery cells.

20. A digital X-ray detector, comprising:
a multi-functional panel support configured to be disposed within a shell assembly of the detector and to support a digital detector array and electronics, to provide power to the detector, and to protect the electronics from radiation damage, wherein the panel support comprises a first enclosure configured to be completely enclosed within the shell assembly and a power source disposed within the first enclosure.

21. The digital detector of claim 20, wherein the panel support is configured to reduce backscattering of X-rays.

22. The digital detector of claim 20, wherein the panel support is configured to provide electromagnetic interference shielding.

23. The digital detector of claim 20, wherein the panel support comprises a second enclosure surrounding the first enclosure and configured to be completely enclosed within the shell assembly, and a support layer disposed between the first and second enclosures.

24. The detector of claim 12, wherein the second enclosure comprises the first side to support a digital detector array and the second side to support the electronics.

* * * * *